United States Patent [19]

Hayashida et al.

[11] Patent Number: 5,291,786
[45] Date of Patent: Mar. 8, 1994

US005291786A

[54] ULTRASONIC MICROSCOPE

[75] Inventors: Mitsumori Hayashida, New Hyde Park, N.Y.; Kiyoshi Fujii, Ina, Japan

[73] Assignee: Olympus Optical Co., Ltd., Tokyo, Japan

[21] Appl. No.: 809,875

[22] Filed: Dec. 18, 1991

[51] Int. Cl.$^5$ .......................................... G01N 29/04
[52] U.S. Cl. ................................................... 73/612
[58] Field of Search ................... 73/602, 606, 612, 620

[56] References Cited

U.S. PATENT DOCUMENTS

| | | | |
|---|---|---|---|
| 3,805,597 | 4/1974 | Ohta et al. | 73/612 |
| 3,818,898 | 6/1974 | Williams | 73/612 |
| 3,996,791 | 12/1976 | Niklas et al. | 73/602 |
| 4,651,568 | 3/1987 | Reich et al. | 73/612 |
| 4,655,084 | 4/1987 | Renzel | 73/612 |
| 4,866,986 | 9/1989 | Cichanski | 73/606 |

FOREIGN PATENT DOCUMENTS

62-87854 4/1987 Japan .

Primary Examiner—Hezron E. Williams
Assistant Examiner—Rose M. Finley
Attorney, Agent, or Firm—Frishauf, Holtz, Goodman & Woodward

[57] ABSTRACT

An ultrasonic microscope of this invention generates a transmission signal from a transmission timing circuit, converts this transmission signal into an ultrasonic pulse, radiates the ultrasonic pulse on a sample, receives an echo from the sample, and generates an electrical echo signal corresponding to the echo. This echo signal is distributed by a distributor to generate a plurality of echo signals. The plurality of echo signals are input to a delay circuit and a gate timing signal generator. The gate timing signal generator generates a gate timing signal with reference to an echo signal exceeding a threshold value. A first gate signal generator generates a first gate signal for determining a first gate period with reference to the transmission timing of the transmission signal. The first gate signal is input to a second gate signal generator. When the gate timing signal is generated within the first gate period, a second gate signal for determining a second gate period is generated with reference to this gate timing signal. A predetermined echo component is extracted by the second gate signal from the echo signal delayed by the delay circuit.

15 Claims, 5 Drawing Sheets

ULTRASONIC MICROSCOPE

BACKGROUND OF THE INVENTION

1. Field of the Invention

The present invention relates to an ultrasonic microscope for observing an internal defect of a sample such as an IC or FRP (Fiber-Reinforced Plastic).

2. Description of the Related Art

A conventional ultrasonic microscope in which only an echo component at a predetermined depth from the surface of a sample can be extracted from an echo reflected from a sample is known. An ultrasonic microscope of this type is described in, e.g., Published Unexamined Japanese Patent Application No. 62-87854.

In this ultrasonic microscope, an ultrasonic pulse generated by a pulse circuit is radiated on a sample, an echo from the sample is received by a reception circuit, and the echo is converted into an electrical echo signal. A trigger signal is generated by the first echo signal having a value exceeding a threshold value when a predetermined period of time elapses from oscillation of the ultrasonic pulse. A gate signal is generated on the basis of this trigger signal. The gate signal is supplied to a gate circuit through which the echo signal is gated. The gate circuit is enabled at a timing and for a period of time determined by the gate signal, thereby extracting an echo component at a predetermined depth from the echo signal.

As described above, since the threshold value is set such that an echo component corresponding to an echo from the surface of the sample exceeds the threshold value for the first time upon oscillation of the ultrasonic pulse, only the echo component at the predetermined depth from the sample surface can be extracted. This echo component is converted into an image to obtain an observation image at the predetermined depth from the sample surface.

An actual time lag of several hundreds of nsec is present from the time when the echo signal from the surface of the sample exceeds the threshold value to the time when the gate circuit is enabled. Each echo from the boundary between the first and second layers inside the sample such as an FRP is reflected with a delay of about 100 nsec from the surface echo.

When the gate signal is generated by using the echo signal from the sample surface as a trigger signal as in the conventional ultrasonic microscope, no echo can be extracted from this boundary. This indicates that an observation image at the boundary between the first an second layers cannot be obtained.

In the conventional ultrasonic microscope described above, the echo from the sample surface cannot be gated, and an observation image on the sample surface cannot be obtained, either.

Figure 5:
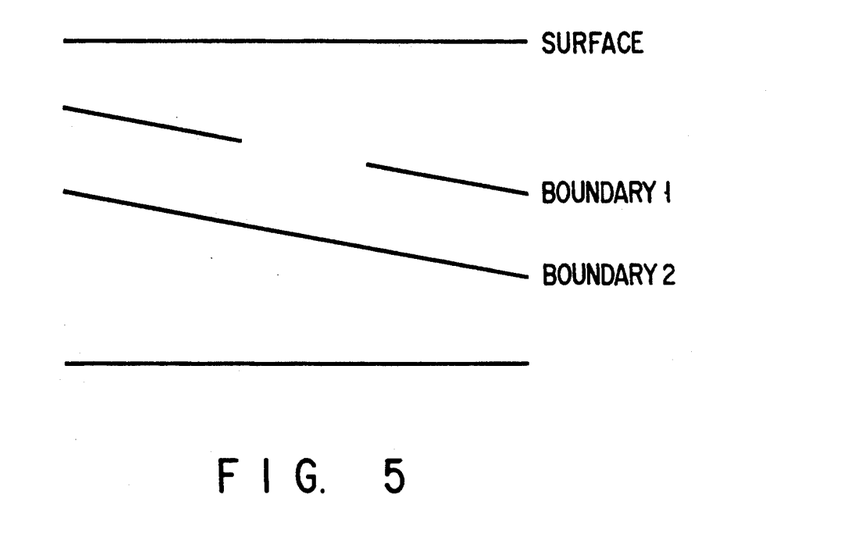
FIG. 5 is a view showing an internal structure of a sample having a boundary inclined with respect to the surface of the sample.

In addition, as shown in FIG. 5, when a target boundary 1 is not present at a predetermined depth from the surface of the sample, an image at the boundary 1 cannot be obtained even if an echo from the sample surface is used as a trigger signal.

In the internal structure shown in FIG. 5, it is preferable that an echo from a boundary 2 is used as a trigger signal, and a previous echo from the boundary 1 is gated using the above trigger signal. The conventional ultrasonic microscope cannot generate such a gate signal.

Figure 6:
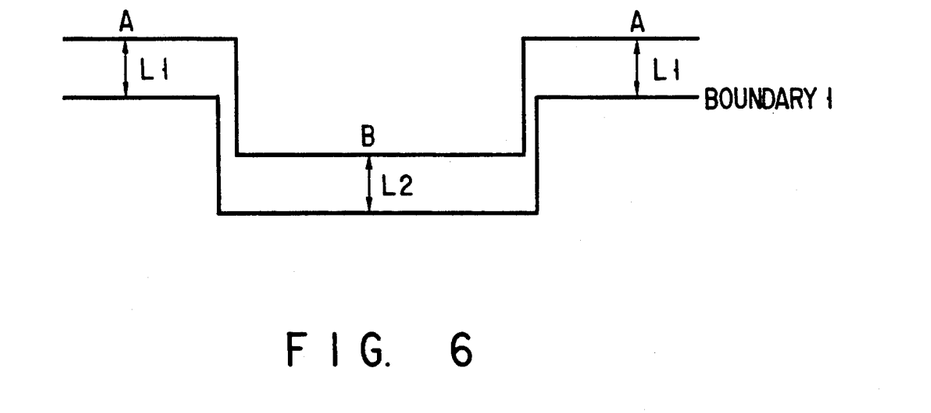
FIG. 6 is a view showing an internal structure of a sample having a stepped boundary.

As shown in FIG. 6, if a boundary in a sample is stepped and condition L1=L2 is established, an echo from a boundary 1 for a portion A returns at the same timing as that for a portion B. Therefore, the resultant images at the portions A and B are the same, resulting in inconvenience.

When no echo returns from the surface of the sample or exceeds the threshold value, a gate signal is generated using internal reflection of an acoustic lens as a trigger signal. As a result, an accurate observation image cannot be obtained.

SUMMARY OF THE INVENTION

The present invention has been made in consideration of the above situation, and has as its object to provide an ultrasonic microscope capable of obtaining an image of a boundary and an image of an arbitrary portion located in a range from the upper surface to the lower surface of the sample even if the boundary inside the sample has a complicated shape.

In order to achieve the above object of the present invention, there is provided an ultrasonic microscope comprising a transmission timing circuit for generating a transmission timing signal at a predetermined transmission timing, an ultrasonic pulse transmitting/receiving unit for converting a transmission signal generated upon reception of the transmission timing signal into an untrasonic pulse and radiating the ultrasonic pulse onto a sample and for receiving an echo from the sample and generating an electrical echo signal corresponding to the echo, a distributor for distributing the echo signal input from the ultrasonic pulse transmitting/receiving unit and outputting a plurality of echo signals having the same level, a delay circuit for receiving one of the plurality of echo signals distributed by the distributor and delaying the input echo signal by a predetermined period of time, a gate timing signal generator for receiving remaining ones of the plurality of echo signals distributed by the distributor, comparing the remaining signals with a preset threshold value, and generating a gate timing signal with reference to an echo signal exceeding the preset threshold value, a first gate signal generator for generating a first gate signal for determining a first gate period with reference to the transmission timing signal generated by the transmission timing circuit, a second gate signal generator for generating a second gate signal for determining a second gate period with reference to the gate timing signal if the gate timing signal is generated within the first gate period, a gate circuit for receiving the echo signal delayed by the delay circuit and enabling a gate during the second gate period of the second gate signal to extract an echo component from the echo signal, and an image forming unit for forming an image of the sample from the echo component extracted from the gate circuit.

With the above arrangement according to the present invention, a first gate signal is generated on the basis of a transmission timing. When an echo signal from a sample exceeds the threshold value, a second gate signal is generated on the basis of an output timing of the gate timing signal. The echo signal delayed by the signal delay circuit and input to the gate circuit is gated by the second gate signal, thereby extracting an arbitrary echo component.

That is, the first gate signal is generated on the basis of the transmission timing. If the echo signal exceeds the threshold value within the gate period of the first gate signal, the second gate signal for extracting the echo component is generated on the basis of the timing when the echo signal exceeds the threshold value. The delay time of the delay circuit and the output timings of the first and second gate signals are adjusted to gate an arbitrary component of the echo signal. Therefore, the arbitrary component including an echo component from the surface of the sample can be extracted.

More specifically, in the ultrasonic microscope having the above arrangement, if the gate timing signal is generated within the first gate period, a plurality of gate signals for determining non-overlapping gate periods are generated with reference to the above gate timing signal.

Image data for a plurality of portions of each sample can be obtained by one operation.

In addition, in the ultrasonic microscope having the above arrangement, when the echo signal input to the gate timing signal generator does not exceed the threshold value within a predetermined period of time and the gate timing signal is not generated within the first gate period, there is further provided a third gate signal generator for generating, with reference to the transmission timing signal, a third gate signal for determining a third gate period within a period for which the echo signal serving as an input to the gate circuit is not present. Therefore, even if an echo signal does not exceed the threshold value within the predetermined period of time, data "0" can be obtained as image data, thereby preventing pixel omissions.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Preferred embodiments of the present invention will be described below.

Figure 1:
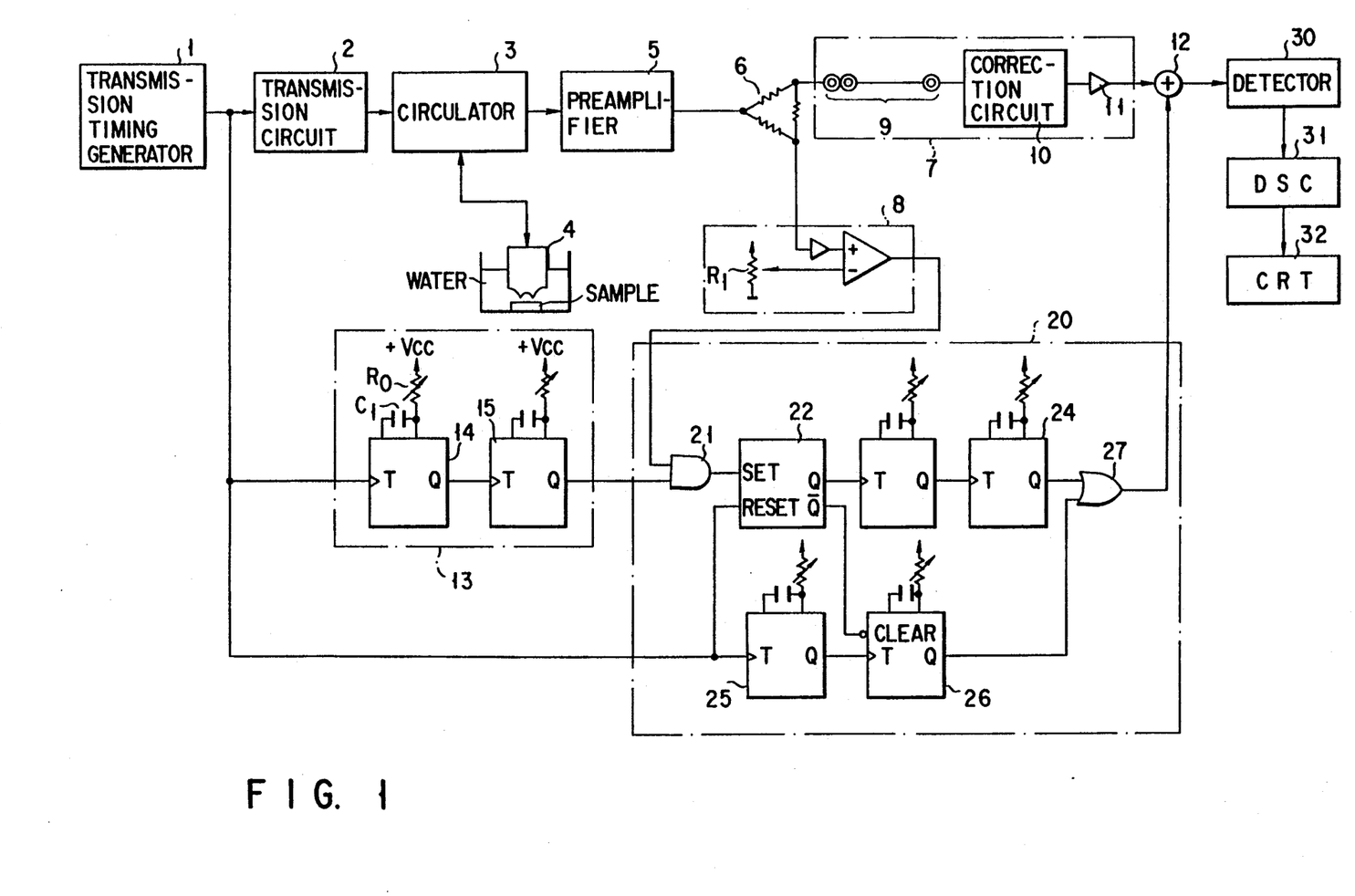
FIG. 1 is a functional block diagram of an ultrasonic microscope according to the first embodiment of the present invention.

FIG. 1 shows an arrangement of an ultrasonic microscope according to the first embodiment of the present invention. In this ultrasonic microscope, a transmission timing signal is output from a transmission timing generator 1 and is input to an ultrasonic transmitting/receiving unit.

The ultrasonic pulse transmitting/receiving unit comprises a transmission circuit 2, a circulator 3, a piezoelectric transducer (not shown), an acoustic lens 4, and a preamplifier 5. In the ultrasonic pulse transmitting/receiving unit, when the transmission timing signal is supplied from the transmission timing generator 1 to the transmission circuit 2, a transmission signal is applied from the transmission circuit 2 to the piezoelectric transducer through the circulator 3. The piezoelectric transducer converts the transmission signal into an ultrasonic pulse. This ultrasonic pulse is radiated on a sample through the acoustic lens 4. The ultrasonic pulse transmitting/receiving unit converts an echo from the sample into an electrical echo signal and outputs the echo signal to the preamplifier 5.

The output terminal of the preamplifier 5 is connected to a distributor 6. The distributor 6 has a function of distributing an input echo signal into a plurality (two in this embodiment) of echo signals having the same level. The distributor 6 is connected to a signal delay circuit 7 and a comparator 8.

The signal delay circuit 7 comprises a cable 9 having a length of about 200 m, a correction circuit 10 for correcting distortion of the amplitude and position of the echo signal during propagation through the cable 9, and a gain variable amplifier 11.

An echo signal delayed by a predetermined period of time by this signal delay circuit 7 is output to a gate circuit 12 serving as a gate means.

The noninverting input (+) terminal of the comparator 8 receives an echo signal from the distributor 6 through the gain variable amplifier 11, and the inverting input (−) terminal of the comparator 8 receives a voltage value corresponding to a threshold value set by a variable resistor R1.

When an echo signal from the distributor 6 exceeds the threshold value, the comparator 8 outputs a gate timing signal.

On the other hand, the transmission timing signal generated by the transmission timing generator 1 is supplied to a first gate generator 13 in addition to the transmission circuit 2.

The first gate generator 13 comprises two series-connected monostable multivibrators 14 and 15. In the first gate generator 13, the first multivibrator 14 sets a period from the time when the transmission timing signal is input to the time when a gate signal (this gate signal will be referred to as a first gate signal hereinafter) is generated. The second multivibrator 15 sets a gate width of the first gate signal. That is, the first gate generator 13 has a function of generating the first gate signal upon reception of the transmission timing signal.

Each of the multivibrators 14 and 15 is adjusted by a resistor $R_0$ and a capacitor $C_1$.

An output from the comparator 8, an output from the first gate generator 13, and a transmission timing signal from the transmission timing generator 1 are supplied to a second gate generator 20.

The second gate generator 20 comprises an AND circuit 21, an RS flip-flop 22, a plurality of monostable multivibrators 23 to 26, and an OR circuit 27. In the second gate generator 20, the output from the comparator 8 and the output from the first gate generator 13 are input to the AND circuit 21.

The RS flip-flop 22, and the multivibrators 23 and 24 are connected in series with the output of the AND circuit 21. An S input to the RS flip-flop 22 receives an output of the AND circuit 21, and an R input to the RS flip-flop 22 receives the transmission timing signal from the transmission timing generator 1.

When the first gate signal and the gate timing signal satisfy an AND condition, i.e., when the gate timing signal is output during a gate period of the first gate signal, a signal of high level is input to the S input of the RS flip-flop 22, and a Q output therefrom is supplied to the multivibrator 23.

A gate signal (to be referred to as a second gate signal hereinafter), a generation timing of which is set by the multivibrator 23 and a gate width of which is determined by the multivibrator 24, is input to one input terminal of the OR circuit 27.

The multivibrators 25 and 26 are connected in series with each other, and the RS flip-flop 22 and the multivibrators 23 and 24 are connected in parallel with each other. A transmission timing signal is input to the multivibrator 25. The multivibrator 26 is operated in response to the output from the multivibrator 25 a predetermined period of time after reception of the transmission timing signal.

An inverted output from the RS flip-flop 22 is input to the clear terminal of the multivibrator 26. That is, when an echo signal does not exceed the threshold value within the gate period of the first gate signal, a third gate signal is input to the other input terminal of the OR circuit 27 upon a lapse of a predetermined period of time with reference to the transmission timing.

The output terminal of the OR circuit 27 is connected to the gate circuit 12. The gate circuit 12 is enabled during the gate widths of the second and third gate signals. During the ON period of the gate circuit 12, an echo component is extracted from the echo signal.

A detector 30 detects the level of the echo component extracted by the gate circuit 12. The extracted echo component data is input to a digital scan converter 31 and converted into image data. A predetermined observation image is displayed on a CRT 32 on the basis of the image data.

An operation of this embodiment will be described with reference to FIG. 2.

A transmission signal is output from the transmission circuit 2 in synchronism with the transmission timing of a transmission timing signal output at a predetermined timing from the transmission timing generator 1. The transmission signal is converted into an ultrasonic pulse, and the ultrasonic pulse is radiated on a sample through the acoustic lens 4.

An echo from the sample is incident on the acoustic lens 4 again and is converted into an electrical echo signal. This echo signal is amplified by the preamplifier 5 and is distributed by the distributor 6. One of a plurality of echo signals distributed by the distributor 6 is input to the comparator 8.

Figure 2:
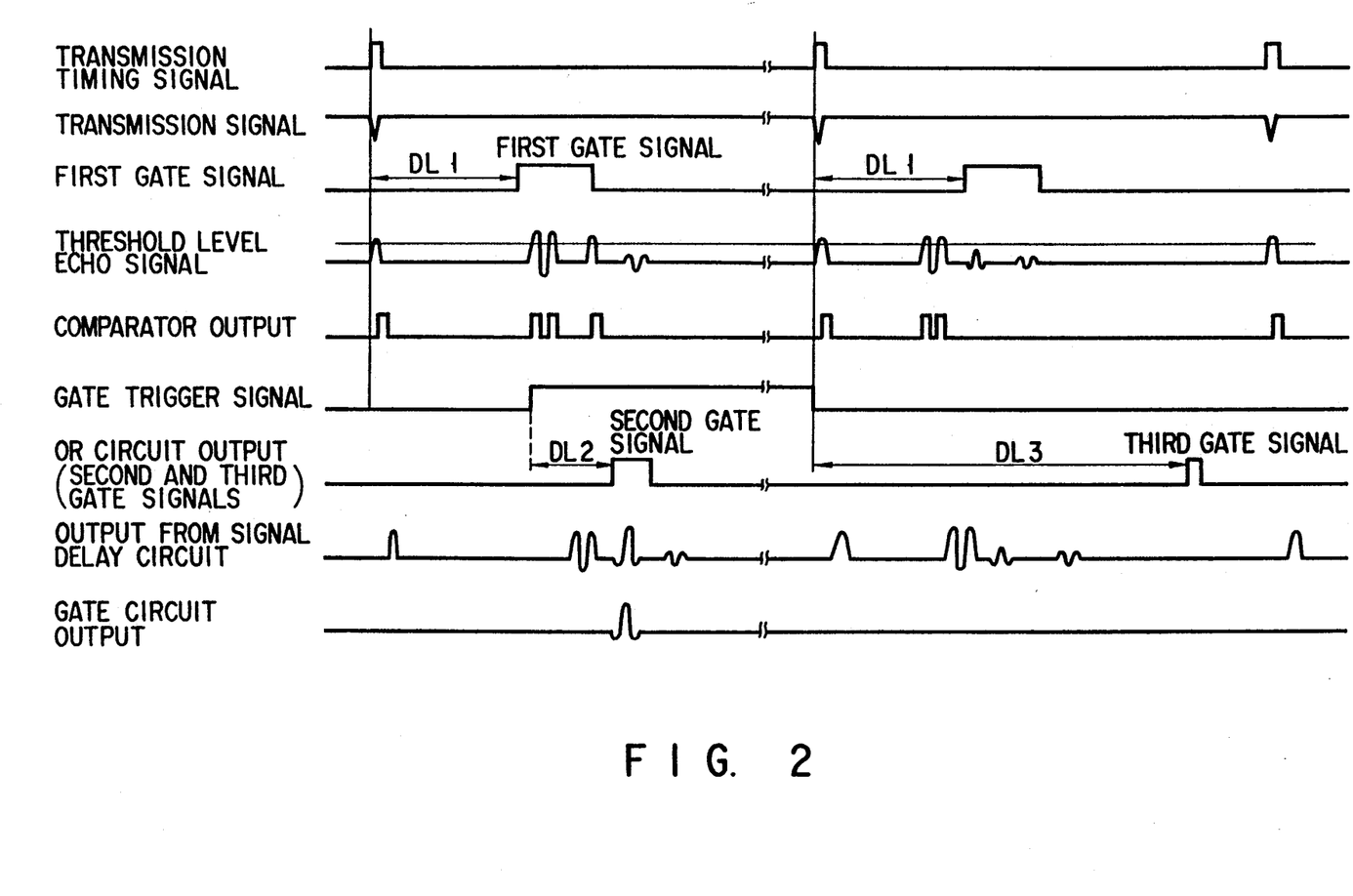
FIG. 2 is a timing chart showing operation timings of the first embodiment.

An echo component from the surface of the sample or a boundary inside the sample has a high level, as shown in FIG. 2. When the threshold level is set in the comparator 8, a comparator output shown in FIG. 2 can be obtained. In this embodiment, a comparator output obtained in response to the first input echo signal exceeding the threshold value during the gate period of the first gate signal serves as the gate timing signal.

On the other hand, the first gate signal is output a predetermined period of time DL1 after the transmission timing signal is output.

In this embodiment, the delay time DL1 is adjusted such that the first gate signal is output in response to an echo component from the sample When the first echo signal exceeding the threshold value is obtained during the gate period of the first gate signal, a gate trigger signal is output from the RS flip-flop 22. When a predetermined period of time DL2 elapses upon output of this gate trigger signal, the second gate signal is output.

By adjusting the output timing of the second gate signal and the delay time of the signal delay circuit 7, an arbitrary component of the echo signal is gated, thereby extracting only an echo component from a predetermined portion of the sample, as shown in FIG. 2.

Detection signals obtained from the detector 30 by peak-holding the echo components are sequentially A/D-converted in response to sampling signals generated on the basis of the trailing edges of the second gate signals. The A/D-converted digital data are received by the digital scan converter 31. A predetermined observation image is displayed on the CRT 32.

When an echo signal does not exceed the threshold value within the gate period of the first gate signal upon output of the transmission timing signal, the third gate signal is output a predetermined period of time DL3 after the transmission timing signal is output, as shown in FIG. 2. A portion having no echoes is gated by the third gate signal. An operation of the digital scan converter 31 is started at a trailing edge of the third gate signal, thereby inputting data "0".

In this embodiment, the first gate generator 13 generates the first gate signal with reference to the transmission timing signal. The second gate signal is generated with reference to a timing when the first echo signal exceeding the threshold value is generated during the gate period of the first gate signal. The echo signal delayed by the signal delay circuit 7 by a predetermined period of time is gated by the second gate signal, thereby extracting the echo component.

For this reason, an echo returning earlier than an echo for triggering the second gate signal can be gated. A fault plane image parallel to an arbitrary reflecting plane can be obtained. For example, even if a sample has a structure shown in FIG. 5, image data at the boundary 1 can be obtained with reference to the echo from the boundary 2.

In this embodiment, the ultrasonic microscope includes the multivibrator 25 started in response to an input transmission timing signal and the multivibrator 26, connected to the multivibrator 25, for receiving an inverted output of the RS flip-flop 22 at its clear terminal. If an echo signal does not exceed the threshold value, the third gate signal is output with reference to the transmission timing signal. Therefore, a gate signal can be generated at a position where no echo is present. Pixel omissions can be prevented, and appropriate A/D conversion timings can be obtained.

Even if a sample has an internal structure shown in FIG. 6, only an image at the boundary A or B can be obtained.

In addition, since the third gate signal is generated even if the echo signal does not exceed the threshold value, generation of a gate signal using internal reflection of a lens as a trigger signal can be appropriately prevented.

The second embodiment of the present invention will be described with reference to FIG. 3.

This embodiment is a modification of the second gate generator of the first embodiment. Only the modified second gate generator will be described below. The same reference numerals as in the ultrasonic microscope shown in FIG. 1 denote the same parts in FIG. 3.

In a gate generator 40 as a modification of the first embodiment, an output from an AND circuit 21 is input to the S terminal of an RS flip-flop 41. A series circuit of multivibrators 23 and 24 and a series circuit of monostable multivibrators 42 and 43 are connected in series with the Q output terminal of the RS flip-flop 41. OR circuits 27 and 44 are connected to the output terminals of the multivibrators 24 and 43, respectively.

Monostable multivibrators 45 and 46 are connected in series with each other. A transmission timing signal is input to the multivibrator 45. An inverted output from the multivibrator 42 is input to the clear terminal of the multivibrator 46. An output from the multivibrator 46 is input to the OR circuits 27 and 44.

A gate signal from the OR circuit 27 is input to a gate circuit 12.

A gate signal from the OR circuit 44 is input to a gate circuit 47.

An echo signal from a signal delay circuit 7 is input to the gate circuits 12 and 47. Outputs from the gate circuits 12 and 47 are output to a CRT 32 through detectors 30 and 48 and digital scan converters 31 and 49.

This gate generator 40 can simultaneously gate a plurality of portions of each echo signal. Echo components from different portions at different depths of the sample can be independently extracted. Image data associated with the respective layer boundaries of a multi-layered sample having a curved surface such as an FRP sample can be simultaneously obtained.

Figure 3:
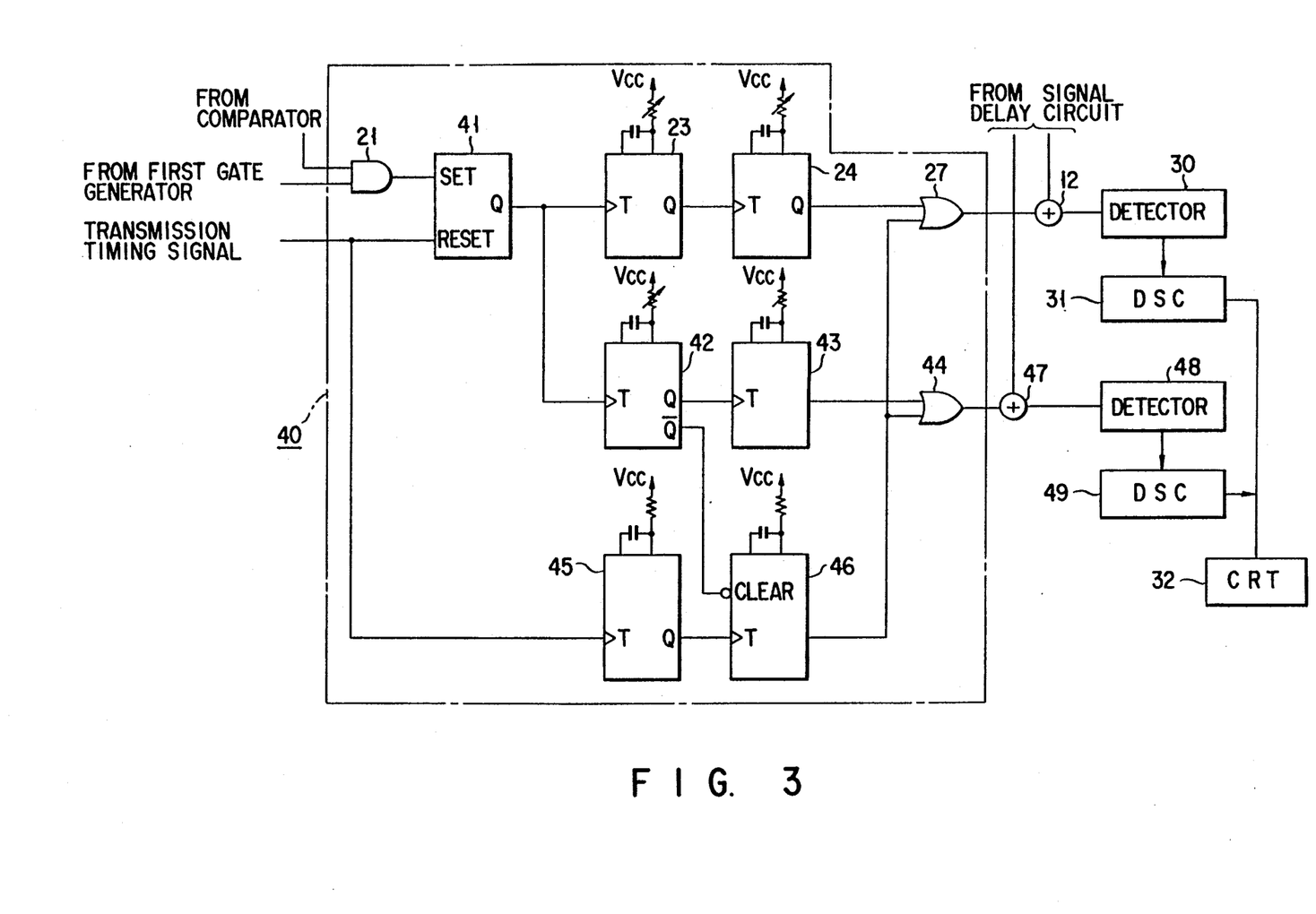
FIG. 3 is a block diagram showing an arrangement of a main part according to the second embodiment of the present invention.

FIG. 3 exemplifies a two-stage arrangement. When the number of stages is increased, an image representing three or more boundaries can be obtained.

Figure 4:
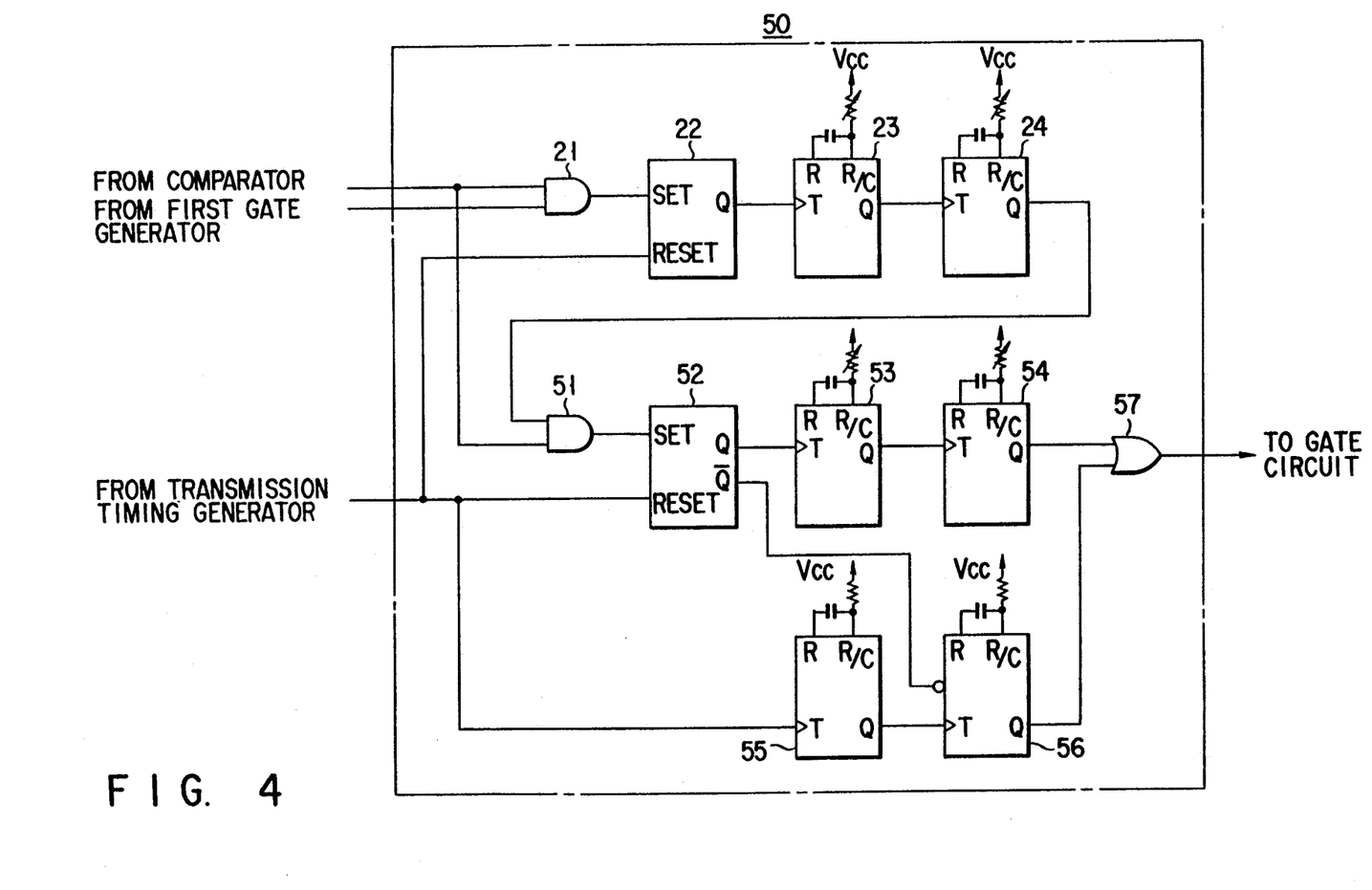
FIG. 4 is a block diagram showing an arrangement of a main part according to the third embodiment of the present invention.

The third embodiment of the present invention will be described with reference to FIG. 4.

The third embodiment is a modification of the second gate generator of the first embodiment as in the second embodiment. Only the second gate generator will be described below.

In a gate generator 50 of the third embodiment, an AND circuit 51, an RS flip-flop 52, monostable multivibrators 53 to 56, and an OR circuit 57 are arranged as in the second gate generator shown in FIG. 1. A second gate signal generated by the AND circuit 21, the RS flip-flop 22, and the multivibrators 23 and 24 as in the first embodiment is input to the AND circuit 51 as a gate timing signal.

This gate generator 50 can sequentially generate gate signals on the basis of echoes from different boundaries within the sample. Even if echo components from different portions are included within the gate period of the second gate signal, only an echo component from a predetermined portion of the sample can be accurately extracted.

As has been described above, according to the present invention, a first gate signal is generated on the basis of a transmission timing of a transmission wave. A second gate signal for extracting an echo component on the basis of echo signals exceeding a threshold value within the gate period of the first gate signal is generated. Gating can be performed with reference to an echo signal from an arbitrary portion of a sample, thereby obtaining an image of a desired portion of the sample.

In addition, a plurality of gate signals are generated on the basis of echo signals exceeding the threshold value within the gate period of the first gate signal, and the echo signals are gated. Therefore, a plurality of images at different depths of the sample can be simultaneously obtained.

Furthermore, when an echo signal does not exceed the threshold value, a third gate signal is generated upon a lapse of a predetermined period of time, and the echo signal is gated. Therefore, pixel omissions and generation of a gate signal on the basis of internal reflection of a lens as a trigger signal can be appropriately prevented.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic microscope comprising:
    transmission timing means for generating a transmission timing signal at a predetermined transmission timing;
    ultrasonic pulse transmitting/receiving means for converting a transmission signal generated upon reception of the transmission timing signal into an ultrasonic pulse and radiating the ultrasonic pulse onto a sample and for receiving an echo from the sample and generating an electrical echo signal corresponding to the echo;
    distributing means for distributing the echo signal input from said ultrasonic pulse transmitting/receiving means and outputting a plurality of echo signals having the same level;
    delay means for receiving one of the plurality of echo signals distributed by said distributing means and delaying the input echo signal by a predetermined period of time;
    gate timing signal generating means for receiving remaining ones of the plurality of echo signals distributed by said distributing means, comparing the remaining signals with a preset threshold value, and generating a gate timing signal with reference to the echo signal exceeding the preset threshold value;
    first gate signal generating means for generating a first gate signal for determining a first gate period with reference to the transmission timing signal generated by said transmission timing means;
    second gate signal generating means for generating a second gate signal for determining a second gate period with reference to the gate timing signal when the gate timing signal is generated within the first gate period;
    gate means for receiving the echo signal delayed by said delay means and enabling a gate during the second gate period of the second gate signal to extract an echo component from the echo signal; and
    image forming means for forming an image of the sample from the echo component extracted from said gate means.

2. A microscope according to claim 1, further comprising means for generating a plurality of gate signals for determining non-overlapping gate periods with reference to the gate timing signal when the gate timing signal is generated within the first gate period, and
    wherein the gate of said gate means is enabled during only the gate periods of the plurality of gate signals to extract different echo components corresponding to echoes from different portions of the sample from the echo signal.

3. A microscope according to claim 1, further comprising third gate signal generating means for generating, with reference to the transmission timing signal, a third gate signal for determining a third gate period in a period for which the echo signal serving as an input to said gate means is not present, when the echo signal input to said gate timing signal generating means does not exceed the threshold value within a predetermined period of time and the gate timing signal is not generated within the first gate period, and  wherein the gate of said gate means is enabled during only the third gate period to receive data "0" as image data, thereby preventing pixel omissions when the echo signal does not exceed the threshold value.

4. An ultrasonic microscope according to claim 1, wherein said ultrasonic transmitting/receiving means comprises:

a transmission circuit for generating the transmission signal upon reception of the transmission timing signal;

a circulator, having first and second input terminals and first and second output terminals, for receiving the transmission signal from said first input terminal and outputting the transmission signal from said first output terminal;

a transducer for converting the transmission signal from said first output terminal of said circulator into an ultrasonic pulse;

an acoustic lens for focusing the ultrasonic pulse converted by said transducer to form a small spot on the sample; and  said transducer electrically converting an echo reflected from the sample and incident on said acoustic lens into the echo signal, supplying the echo signal to said second input terminal of said circulator, and causing the echo signal to be output from said second output terminal of said circulator to said distributing means.

5. A microscope according to claim 1, wherein said delay means comprises a cable having a length enough to delay the echo signal from said distributing means by a predetermined period of time, the echo signal being delayed by the predetermined period of time through said cable.

6. A microscope according to claim 5, wherein said delay means includes correcting means for correcting the echo signal in order to eliminate distorted components produced when the echo signal propagates through said cable.

7. A microscope according to claim 1, wherein said gate timing signal generating means comprises:

a variable resistor for setting a threshold voltage representing the threshold value; and  a comparator, having first and second input terminals, for receiving an echo signal from said distributing means at said first input terminal and for receiving the threshold voltage from said variable resistor at said second input terminal.

8. A microscope according to claim 1, wherein said first gate signal generating means comprises:

a first monostable multivibrator for receiving the transmission timing signal and generating an output signal when a predetermined period of time elapses upon reception of the transmission timing signal, the predetermined period of time being a period from a timing when the transmission timing signal is output to a timing when the first gate signal is output; and  a second monostable multivibrator for receiving an output signal from said first monostable multivibrator and generating the first gate signal during a given period from a timing when the output signal from said first monostable multivibrator is input to a timing when a predetermined period of time elapses therefrom, the given period corresponding to a first gate width of the first gate signal.

9. A microscope according to claim 1, wherein said second gate generating means comprises:

AND gate means for receiving the first gate signal and the gate timing signal and outputting an AND signal of the first gate signal and the gate timing signal;

an RS flip-flop having an S input terminal for receiving an output signal from said AND gate means, an R input terminal for receiving the transmission timing signal, and a Q output terminal for outputting the signal received at said S input terminal;

a first monostable multivibrator for receiving an output signal from said Q output terminal of said RS flip-flop and generating an output signal when a predetermined period of time elapses upon reception of the output signal from said Q output terminal, the predetermined period of time corresponding to a generation timing of the second gate signal; and  a second monostable multivibrator for receiving an output signal from said first monostable multivibrator and generating the second gate signal during a given period from a timing when the output signal from said first monostable multivibrator is input to a timing when a predetermined period of time elapses therefrom, the given period corresponding to a gate width of the second gate signal.

10. A microscope according to claim 3, wherein said third gate signal generating means comprises:

a first monostable multivibrator for receiving the transmission timing signal and generating an output signal when a predetermined period of time elapses upon reception of the transmission timing signal, the predetermined period of time corresponding to a generation timing of the third gate signal;

a second monostable multivibrator for receiving an output signal from said first monostable multivibrator and generating, when the gate timing signal is not generated, the third gate signal during a given period from a timing when the output signal from said first monostable multivibrator is input to a timing when a predetermined period of time elapses therefrom, the given period corresponding to a gate width of the third gate signal; and  OR gate means for receiving the third gate signal from said second monostable multivibrator and the second gate signal from said second gate signal generating means and outputting an OR signal of the second gate signal and the third gate signal to said gate means.

11. A microscope according to claim 1, further comprising third gate signal generating means and wherein said second gate signal generating means comprises:

AND gate means for receiving the first gate signal and the gate timing signal and outputting an AND signal of the first gate signal and the gate timing signal;

RS flip-flop having an S input terminal for receiving an output signal from said AND gate means, an R input terminal for receiving the transmission timing signal, a Q output for outputting the signal received at said S input terminal, and a Q output terminal for outputting an inverted signal of the signal received at said S input terminal;

a first monostable multivibrator for receiving the output signal from said Q output terminal of said RS flip-flop and generating an output signal when a predetermined period of time elapses upon reception of the output signal from said Q output terminal, the predetermined period of time corresponding to a generation timing of the second gate signal;

a second monostable multivibrator for receiving the output signal from said first monostable multivibrator and generating the second gate signal during a given period from a timing when the output signal from said first monostable multivibrator is input to a timing when a predetermined period time elapses therefrom, the given period corresponding to a gate width of the second gate signal;

said third gate signal generating means being provided with a third monostable multivibrator for receiving the transmission timing signal and generating an output signal when a predetermined period of time elapses upon reception of the transmission timing signal, the predetermined period of time corresponding to a generation timing of the third gate signal;

a fourth monostable multivibrator for receiving the output signal from said third monostable multivibrator, generating the third gate signal during a given period from a timing when the output signal from said third monostable multivibrator is input to a timing when a predetermined period of time elapses therefrom, the predetermined period of time corresponding to a gate width of the third gate signal, receiving an inverted output from said RS flip-flop, and stopping generation of the third gate signal in response to the inverted output; and OR gate means for receiving the third gate signal and the second gate signal and outputting an OR signal of the second and third gate signals to said gate means.

12. An ultrasonic microscope comprising:

transmission timing means for generating a transmission timing signal at a predetermined transmission timing;

ultrasonic pulse transmitting/receiving means for converting a transmission signal generated upon reception of the transmission timing signal into an ultrasonic pulse and radiating the ultrasonic pulse onto a sample and for receiving an echo from the sample and generating an electrical echo signal corresponding to the echo;

distributing means for distributing the echo signal input from said ultrasonic pulse transmitting/receiving means and outputting a plurality of echo signals having the same level;

delay means for receiving one of the plurality of echo signals distributed by said distributing means and delaying the input echo signal by a predetermined period of time;

gate timing signal generating means for receiving remaining ones of the plurality of echo signals distributed by said distributing means, comparing the remaining signals with a preset threshold value, and generating a gate timing signal with reference to the echo signal exceeding the preset threshold value;

first gate signal generating means for generating a first gate signal for determining a first gate period with reference to the transmission timing signal generated by said transmission timing means;

second gate signal generating means for generating a plurality of gate signals for determining non-overlapping gate periods with reference to the gate timing signal when the gate timing signal is generated within the first gate period;

a plurality of gate circuits for receiving the echo signal delayed by said delay means and the plurality of gate signals generated by said second gate signal generating means to enable a plurality of gates during the gate periods of the plurality of gate signals, thereby extracting a plurality of different echo components corresponding to echoes from different portions of the sample from the echo signal; and image forming means for forming an image of the sample from the echo components extracted by said gate circuits.

13. A microscope according to claim 12, wherein said second gate signal generating means comprises:

AND gate means for receiving the first gate signal and the gate timing signal and outputting an AND signal of the first gate signal and the gate timing signal;

an RS flip-flop having an S input terminal for receiving an output signal from said AND gate means, an R input terminal for receiving the transmission timing signal, and a Q output terminal for outputting the signal received at said S input terminal;

a first multivibrator group including a plurality of monostable multivibrators each for receiving an output signal from said Q output terminal of said RS flip-flop and generating an output signal when a predetermined period of time elapses upon reception of the output signal from said Q terminal, the predetermined period of time corresponding to a generation timing of the gate signal; and a second multivibrator group including a plurality of monostable multivibrators each for receiving an output signal from a corresponding monostable multivibrator of said first multivibrator group and generating a gate signal during a given period from a timing when the output signal from said corresponding monostable multivibrator is input to a timing when a predetermined period of time elapses therefrom, the given period corresponding to a gate width of a corresponding one of the gate signals.

14. A microscope according to claim 12, further comprising third gate signal generating means for generating, with reference to the transmission timing signal, a third gate signal for determining a third gate period in a period for which the echo signal serving as an input to each gate circuit is not present, when the echo signal input to said gate timing signal generating means does not exceed the threshold value and the gate timing signal is not generated within the first gate period, and wherein the gate of each gate circuit is enabled within only the third gate period to receive data "0" as image data, thereby preventing pixel omissions when the echo signal does not exceed the threshold value.

15. A microscope according to claim 14, wherein said third gate signal generating means comprises:

a first monostable multivibrator for receiving the transmission timing signal and generating an output signal when a predetermined period of time elapses upon reception of the transmission timing signal, the predetermined period of time corresponding to a generation timing of the third gate signal;

a second monostable multivibrator for receiving the output signal from said first monostable multivibrator and generating, when the gate timing signal is not generated, the third gate signal during a given period from a timing when the output from said first monostable multivibrator is input to a timing when a predetermined period of time elapses therefrom, the given period corresponding to a gate width of the third gate signal; and OR gate means including a plurality of gate circuits each for receiving the third gate signal from said second monostable multivibrator and a corresponding one of the gate signals from said second gate signal generating means, and outputting an OR signal of the third gate signal and the corresponding gate signal to the corresponding gate circuit.

* * * * *